United States Patent
Tapper et al.

(10) Patent No.: US 10,022,554 B2
(45) Date of Patent: Jul. 17, 2018

(54) LIGHT THERAPY BANDAGE SYSTEM

(71) Applicant: Johnson & Johnson Consumer Inc., Skillman, NJ (US)

(72) Inventors: Jay Tapper, Wayne, PA (US); Lawrence A Blaustein, Chagrin Falls, OH (US); David Shuter, Palm Beach Gardens, FL (US); Charles Peter Althoff, New York, NY (US); Jeff Michaelson, Huntington Woods, MI (US); Bradley Feild Craddock, Brooklyn, NY (US)

(73) Assignee: Johnson & Johnson Consumer Inc., Skillman, NJ (US)

(*) Notice: Subject to any disclaimer, the term of this patent is extended or adjusted under 35 U.S.C. 154(b) by 0 days.

(21) Appl. No.: 14/212,601

(22) Filed: Mar. 14, 2014

(65) Prior Publication Data

US 2014/0277298 A1    Sep. 18, 2014

Related U.S. Application Data

(60) Provisional application No. 61/791,738, filed on Mar. 15, 2013.

(51) Int. Cl.
*A61N 5/06* (2006.01)
*A61B 17/00* (2006.01)
*A61B 18/00* (2006.01)

(52) U.S. Cl.
CPC .. *A61N 5/0616* (2013.01); *A61B 2017/00057* (2013.01); *A61B 2017/00084* (2013.01);
(Continued)

(58) Field of Classification Search
CPC ......... A61F 13/023; A61F 2013/00919; A61K 41/0057; A61N 5/062; A61N 5/0616; A61N 2005/0645
(Continued)

(56) References Cited

U.S. PATENT DOCUMENTS

| 5,824,023 | A | 10/1998 | Anderson |
| 6,045,575 | A | 4/2000 | Rosen et al. |

(Continued)

FOREIGN PATENT DOCUMENTS

| CN | 1738663 A | 2/2006 |
| WO | WO2004052238 | 12/2003 |
| WO | WO2011049419 | 10/2010 |

OTHER PUBLICATIONS

International Search Report for PCT/US2014/035009, dated Sep. 23, 2014.
(Continued)

*Primary Examiner* — William Thomson
*Assistant Examiner* — Dacheng Xie
(74) *Attorney, Agent, or Firm* — Fay Sharpe LLP

(57) ABSTRACT

The radiant energy bandage system is disclosed including a plurality of therapeutic lamps and a controller for operating the lamps. Batteries power the lamps and are secured to a flexible fabric layer supporting the lamps and the controller. A foam and reflective layer includes a spacer foam and radiant energy reflector. A plurality of spacer windows are aligned with the lamps for communicating lamp radiation therethrough. A sheer mesh fabric layer is supposed to cover the foam and reflective layer.

16 Claims, 8 Drawing Sheets

(52) U.S. Cl.
CPC .............. *A61B 2018/00642* (2013.01); *A61B 2018/00791* (2013.01); *A61B 2018/00988* (2013.01); *A61N 2005/0626* (2013.01); *A61N 2005/0627* (2013.01); *A61N 2005/0645* (2013.01); *A61N 2005/0651* (2013.01); *A61N 2005/0652* (2013.01); *A61N 2005/0654* (2013.01); *A61N 2005/0659* (2013.01); *A61N 2005/0663* (2013.01); *A61N 2005/0665* (2013.01); *A61N 2005/0666* (2013.01)

(58) Field of Classification Search
USPC ...................................................... 607/88–92
See application file for complete search history.

(56) References Cited

U.S. PATENT DOCUMENTS

| | | | |
|---|---|---|---|
| 6,350,275 | B1 | 2/2002 | Vreman |
| 6,508,813 | B1 | 1/2003 | Altshuler |
| 6,511,475 | B1 | 1/2003 | Altshuler et al. |
| 6,517,532 | B1 | 2/2003 | Altshuler et al. |
| 6,689,380 | B1 | 2/2004 | Marchitto et al. |
| 6,743,249 | B1 | 6/2004 | Alden |
| 6,824,265 | B1 | 11/2004 | Harper |
| 6,860,896 | B2 | 3/2005 | Leber et al. |
| 7,125,416 | B2 | 10/2006 | Kent et al. |
| 7,438,409 | B2 | 10/2008 | Jordan |
| 7,824,241 | B2 | 11/2010 | Duprey |
| 7,896,908 | B2 | 3/2011 | Ripper et al. |
| 8,192,473 | B2 | 6/2012 | Tucker et al. |
| 8,252,033 | B2 | 8/2012 | Tucker et al. |
| 8,491,118 | B2 | 7/2013 | Waters |
| 8,858,607 | B1 | 10/2014 | Jones |
| 2002/0143373 | A1 | 10/2002 | Courtnage et al. |
| 2003/0009205 | A1* | 1/2003 | Biel ................ A61N 5/0601 607/88 |
| 2003/0167080 | A1 | 9/2003 | Hart et al. |
| 2003/0199800 | A1 | 10/2003 | Levin |
| 2004/0138726 | A1 | 7/2004 | Savage, Jr. et al. |
| 2004/0162549 | A1 | 8/2004 | Altshuler |
| 2005/0182460 | A1* | 8/2005 | Kent ................ A61N 5/0616 607/88 |
| 2006/0173514 | A1 | 8/2006 | Biel et al. |
| 2007/0239232 | A1* | 10/2007 | Kurtz ................ A61N 5/0613 607/87 |
| 2008/0058915 | A1 | 3/2008 | Chang |
| 2009/0192437 | A1 | 7/2009 | Soltz et al. |
| 2010/0023927 | A1 | 1/2010 | Yang et al. |
| 2011/0054573 | A1 | 3/2011 | Mitchell |
| 2012/0116485 | A1 | 5/2012 | Burgmann |
| 2012/0323064 | A1 | 12/2012 | Kim |
| 2014/0074010 | A1* | 3/2014 | Veres ................ A61N 5/06 604/20 |

OTHER PUBLICATIONS

PCT/US2014/069789—PCT Notification Concerning Transmittal of Int'l Preliminary Report on Patentability dated Jun. 23, 2016 (Johnson & Johnson Consumer, Inc.).

PCT/US2016/038606—PCT Notification Concerning Transmittal of Int'l Preliminary Report on Patentability dated Nov. 15, 2016 (Johnson & Johnson Consumer, Inc.).

PCT/US2016/038607—PCT Notification Concerning Transmittal of Int'l Preliminary Report on Patentability dated Sep. 29, 2016 (Johnson & Johnson Consumer, Inc.).

PCT/US2016/038608—PCT Notification Concerning Transmittal of Int'l Preliminary Report on Patentability dated Sep. 29, 2016 (Johnson & Johnson Consumer, Inc.).

PCT/US2016/038612—PCT Notification Concerning Transmittal of Int'l Preliminary Report on Patentability dated Sep. 29, 2016 (Johnson & Johnson Consumer, Inc.).

PCT/US2014035009; Extended European Search Report; 8 pages, J&J Consumer Inc., Munich, dated Dec. 14, 2016.

* cited by examiner

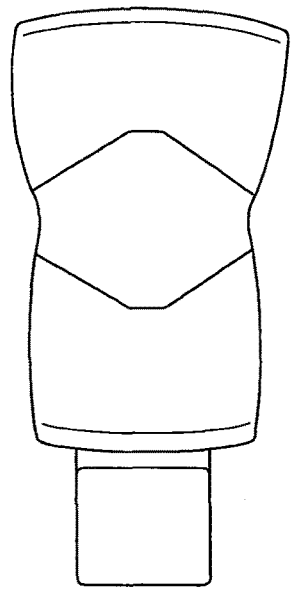
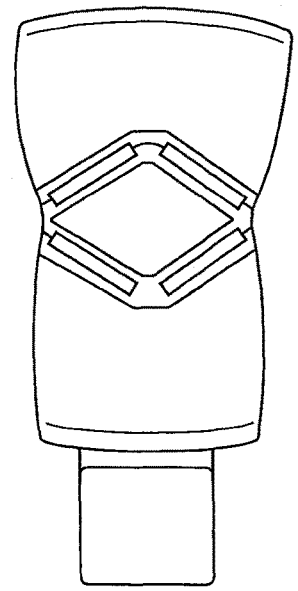
FIG. 4A　　　FIG. 4B
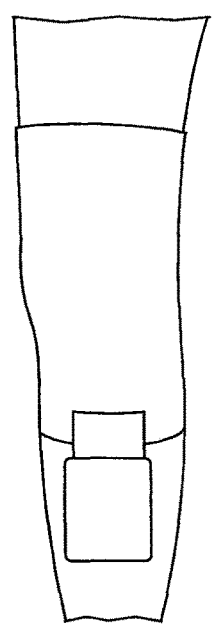
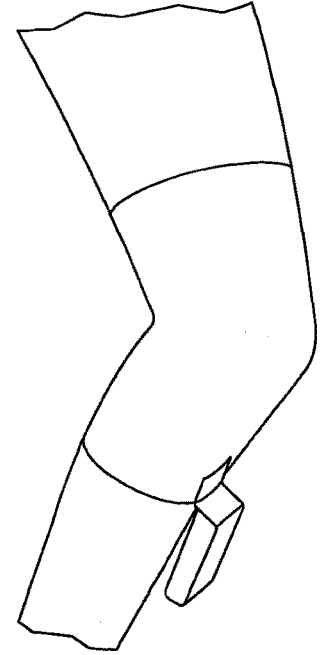
FIG. 4C　　　FIG. 4D

LIGHT THERAPY BANDAGE SYSTEM

This application claims the priority benefit of U.S. application Ser. No. 61/791,738, filed Mar. 15, 2013, the disclosure of which is incorporated herein by reference.

INCORPORATION BY REFERENCE

"Light Therapy Platform System", U.S. Patent Publication No. US 2013-0066404 A1, published on Mar. 14, 2013, by Tapper et al., the disclosure of which is incorporated herein by reference in its entirety.

FIELD

The present embodiments relate to devices and methods for delivering light-based skin therapy treatments for improving skin health, and/or relieving subdermal tissue using light-emitting diode (LED) light therapy, although other types of light radiating sources can be used.

BACKGROUND

Certain light spectrums emitted by LEDs (blue or red) are known to be therapeutic for skin treatment by being beneficial to better factor wound healing or relieving muscular or other subdermal tissue pain. However, there is a need to provide users/patients with a convenient at-home light therapy delivery device such as a wearable bandage that is adjustable or flexible to conform to different sizes and shapes, and that is simple to use without user discomfort. The alternative is visiting a doctor's office to receive treatments.

Prior known light therapy devices have suffered from problems relating to the exposure of the LEDs and the associated circuitry to power the LEDs to contact by users. More particularly, in an effort to maximize light communication to a patient, the LEDs have been disposed in a manner which allow them to be physically engaged (e.g., touched) by a patient, or even contact a treatment surface, which processes are debilitating to the LEDs as a result of the accumulation of dirt and oil. In addition, any such engagement can be dangerous to patients who are exposed to the sharp or hot edges of the LEDs and the associated circuitry. The exposure of detailed circuitry presents an intimidating and unpleasant experience.

Another problem with prior known devices is that the LED arrangement is fixed and not adjustable to better correspond to would location, size or shape, or to be better placed relative to pain areas. The LEDs of such devices are not selectively arrangeable in a variety of patterns to better go near particular pain areas of a wound.

It is desired to provide alternative means of using the benefits of the light therapy in a manner to maximize therapeutic efficiencies in exposure while maintaining ease and convenience of use. For this reason, a variety of light weight, flexible and adjustable embodiments are disclosed within this disclosure incorporating a variety of energy varying applications responsive to user conditions or needs.

SUMMARY

The present embodiments comprise phototherapy systems and devices comprising a therapeutic lamp platform for radiant lamps such as LEDs which are disposed in an assembly comprising a multi-layer structure wherein the LEDs are guarded from patient contact.

The present embodiments comprise an adjustable/flexible platform for providing a light-based therapy that is adaptable to the user's receptive surfaces, whether based on size or condition, wherein the light therapy can be applied without limitation of the kind of light and without limitation of the ultimate purpose of the therapy, i.e., beauty, health, pain relief and/or wound healing. Such sources can vary in the form of the radiant energy delivery. Pulsed light (IPL), focused light (lasers) and other methods of manipulating light energy are encompassed within the present embodiments. Other methods of light emission may comprise continuous, pulsed, focused, diffuse, multi wavelength, single wavelength, visible and/or non-visible light wavelengths.

A present embodiment describes forms such as a shaped/fitted bandage with LED light emitted from LED bulbs or LED strips that are capable of being adjusted to accommodate the variances in the desired treatment area.

The present disclosure thus describes a fully flexible and adjustable LED device which provides improved usability and light dispersion. Such device comprises light therapy bandage system including a spacing and insulating layer to effectively elevate the lamp radiation from the treatment area (e.g. skin) of the patient's last user. The lamps are recessed relative to the insulating layer and further covered by a sheer mesh layer to protect the user from being able to contact the lamps.

BRIEF DESCRIPTION OF THE DRAWINGS

FIG. 4A is a perspective view of another embodiment comprising a knee brace;

FIG. 4B is an alternative view of the device of 4A;

FIG. 4C is an alternative view of the device of 4A;

FIG. 4D is an alternative view of the device of 4A;

DETAILED DESCRIPTION

The subject embodiments relate to a phototherapy system including methods and devices, preferably comprising a wearable device with a removable, portable battery pack for powering therapeutic lamps in the device. The subject devices display numerous benefits including a light platform wherein the platform and the lamps therein are properly positionable relative to a user during use with no human touch. That is, structural componentry of the device not only supports the lamp platform on the user, but functions as a guide for the appropriate disposition of the lamps relative to the treatment areas of the user. The structural assembly of the device precludes sharp or hot surfaces from being engageable by a user as the lamps are recessed relative to an inner reflective surface nearer to and facing the patient treatment surface. Circuit componentry to communicate power to the lamps is also encased within the flexible wall structure. Therapeutic light, shining through wall apertures or mesh, is communicated to the user while the lamps and the circuitry are effectively covered within the layered wall structure. A surface is thus presented to the user that is properly spaced for the desired therapeutic treatments, yet provides improved ventilation so that an aesthetic and appealing device surface is presented to the user that minimizes user discomfort. Other benefits relate to the adjustability of the device in the form of a bandage which forms upon user receipt to match a treatment surface, e.g., back or knee, of the user. The overall assembly is purposefully constructed of relatively light weight and minimized componentry for ease of user use and comfort.

Figure 1A:
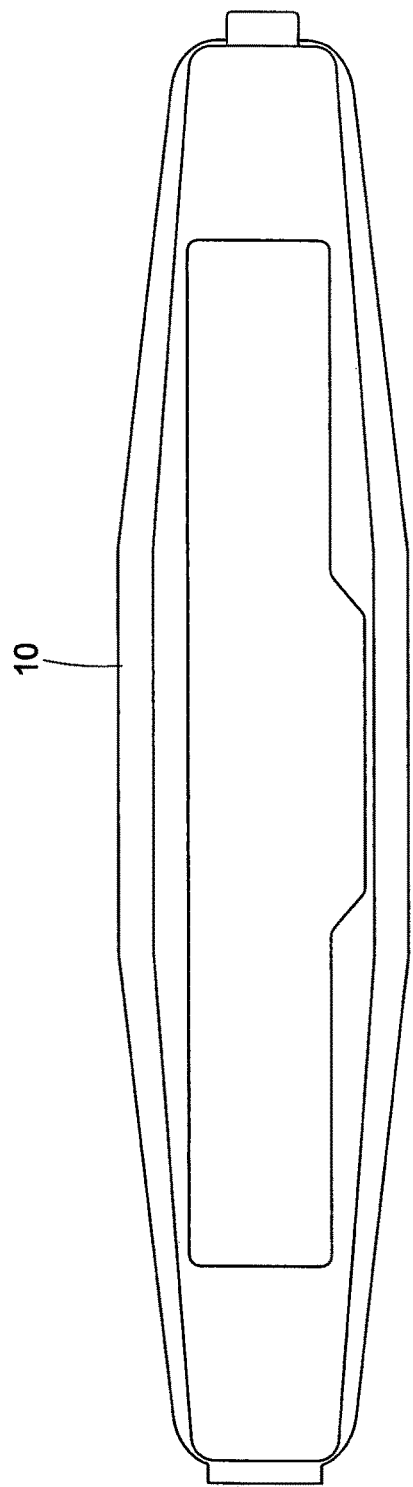
FIG. 1A is a plan view of one embodiment of a therapeutic lamp platform comprising a lumbar brace.
Figure 1B:
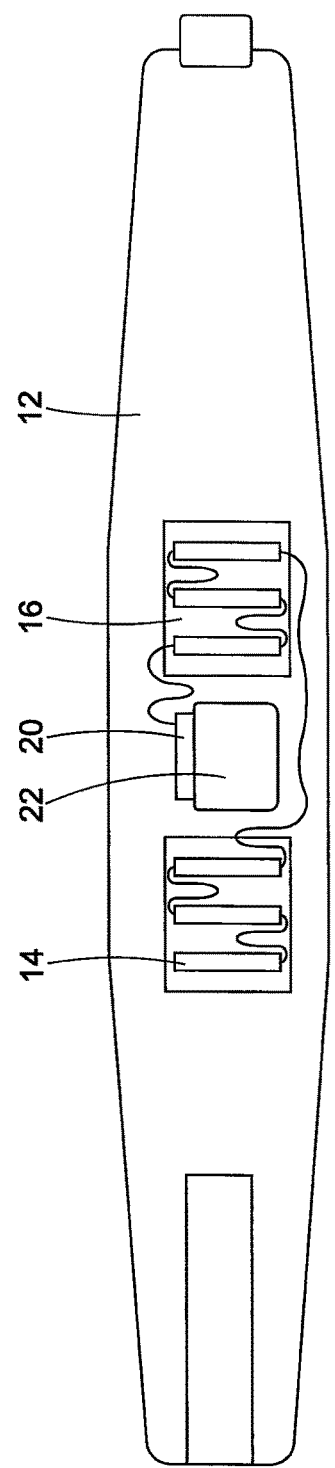
FIG. 1B is an opposite plan view of the device of FIG. 1A.
Figure 2:
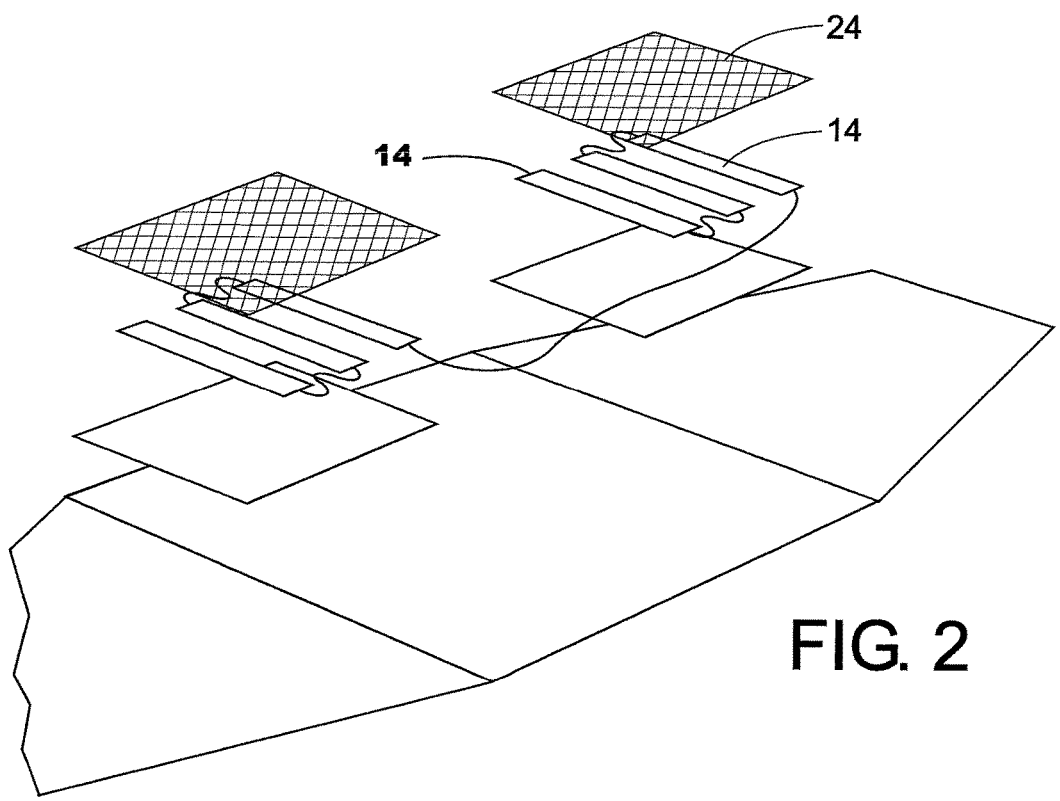
FIG. 2 is an exploded view of the device of FIGS. 1A and 1B.
Figure 3:
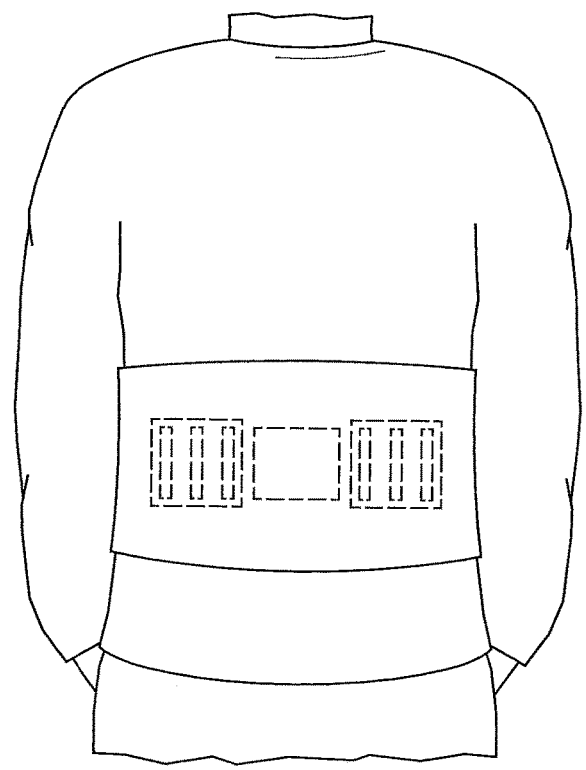
FIG. 3 is a perspective view of the device of FIGS. 1A and 1B on a patient.

More particularly, and with reference to FIGS. 1A, 1B and 2, the subject embodiments preferably comprise a lumbar brace 10 that can be worn by a patient/user such as shown in FIG. 3. The brace 10 can be supported and affixed on the user by a hook-and-loop locking fabric at the terminal ends of the brace. Such a brace will typically include heat wraps for lower back and hips 14 on the exterior of the brace 10 opposite of the patient facing surface. The LED platform of the bandage comprises an elastic member 12 on which LED strips 14 are mounted on a support layer 16 that is heat insular and/or reflective. It is important that the layer 16 be flexible and stretchable with the elastic bandage 12. Note that the wires connecting the LEDs to the battery pouch 22 are of extra length to allow stretching of the dimension between the LED strips. Power is supplied by a battery pack 20 received in the battery pouch 22. The LED lights 14 are spaced from direct engagement of the patient by an insular layer 24 which can range from a mesh cloth to a flexible sheet of formable material in which the strips are integrally molded.

In one embodiment the mesh cloth allows communication of the lamp radiation through to the patient without reflection.

In another embodiment the flexible formable material 24 can have apertures (not shown) functioning as a window to allow the light to pass through and the remainder can be of a light reflective surface. In this embodiment the LEDs are effectively hidden from the patient, where layer 24 is a mesh cloth that the patient can, of course, see the LEDs tips and the associated circuitry.

The subject system may also include control systems to vary light intensity, frequency or direction. A portable battery pack is included.

The subject adjustability may be implemented through "smart" processing and sensor systems for enhanced flexibility/adjustability in the form of adjustable energy output, adjustable wavelengths, priority zones, timers, and the like. The sensors of the sensor systems will enable the subject embodiments to have the ability to evaluate the treatment area and plan a smart treatment, utilizing more or less energy on the priority zones. The subject embodiments can be smart from the standpoint of body treatment area such as knee or back, and of skin type, age, overall severity of problems and have the ability to customize the treatment accordingly.

In yet another embodiment, the lamps are embedded in a flexible sheet of formable material and are integrally molded as strips within a material sheet.

Figure 5:
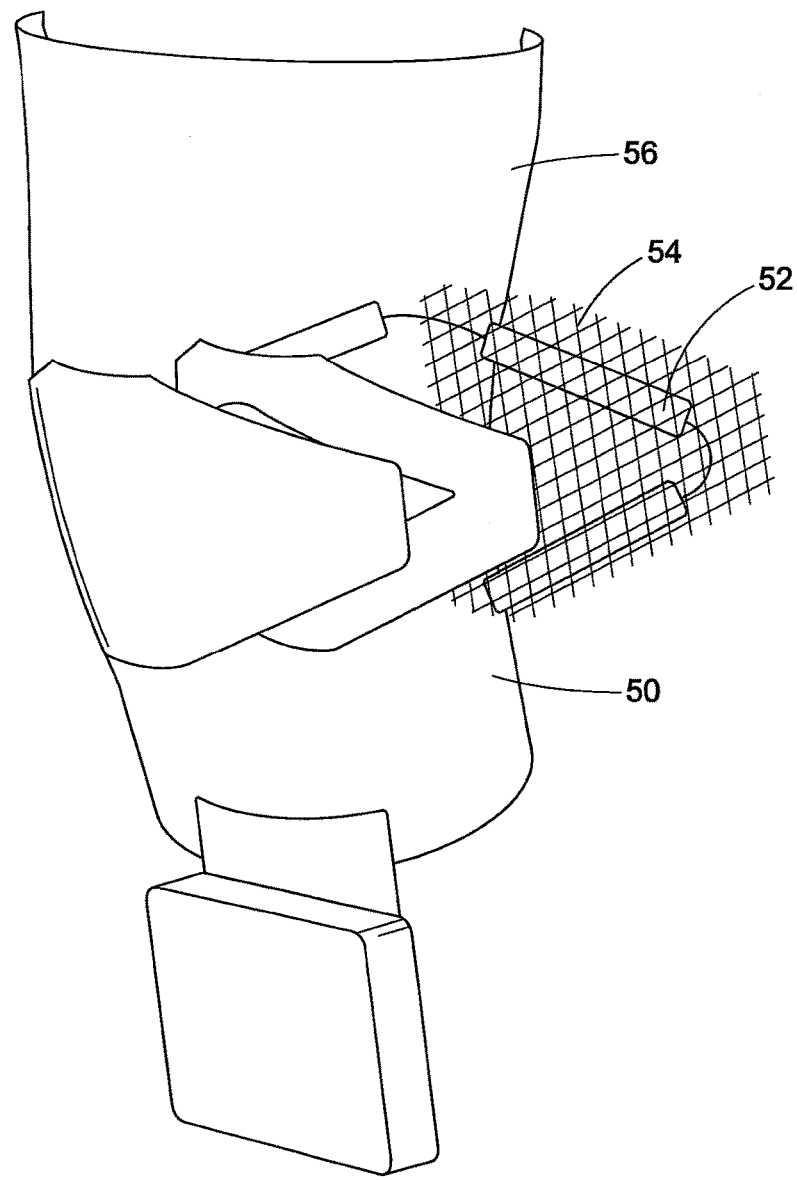
FIG. 5 is an exploded perspective view of the device of FIG. 4A.

With reference to FIGS. 4A, 4B, 4C, 4D and 5, the LED bandage is shown where the LED strips are arranged in a diamond pattern and the elastic bandage is formed as a unitary sleeve which is pulled over the leg to the knee area. The multi-structural layer of the brace is shown in FIG. 5 to comprise an elastic bandage platform 50, a first layer reference material that may be constructed of emergency blanket material 52, LED light strips 54, and a surface layer 56 to cover the strips 54.

Figure 7:
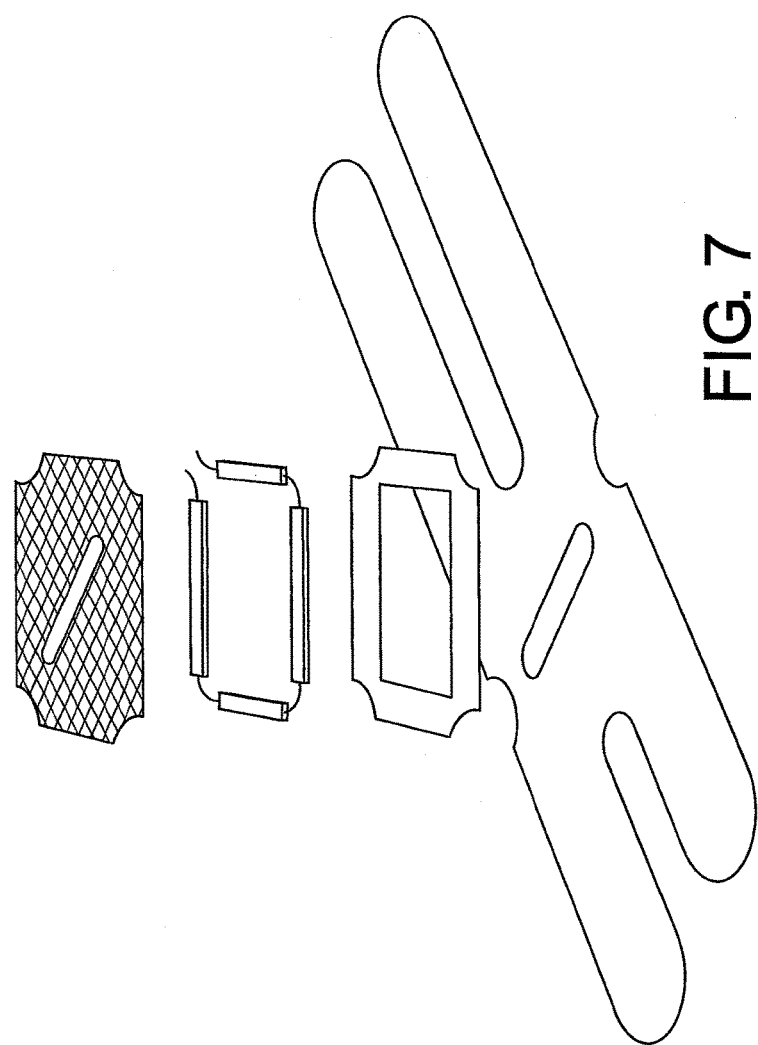
FIG. 7 is an exploded view of the device of FIG. 6.
Figure 6:
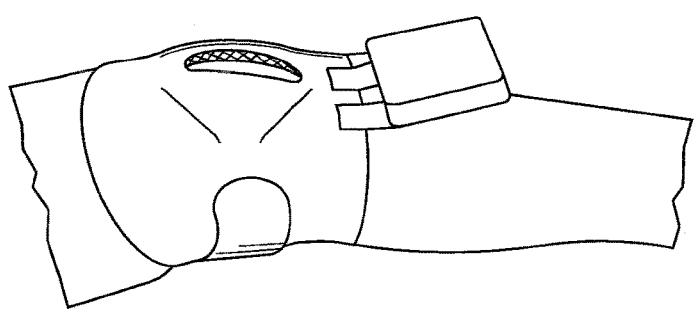
FIG. 6 is an alternative embodiment of a knee brace.

With reference to FIGS. 6 and 7, another alternative embodiment of a knee brace is shown where the elastic bandage is a wraparound of the knee as it is shown in FIG. 6 again in a diamond pattern about the patient's kneecap including the multi-layer structures such as is shown in FIG. 7.

Figure 8:
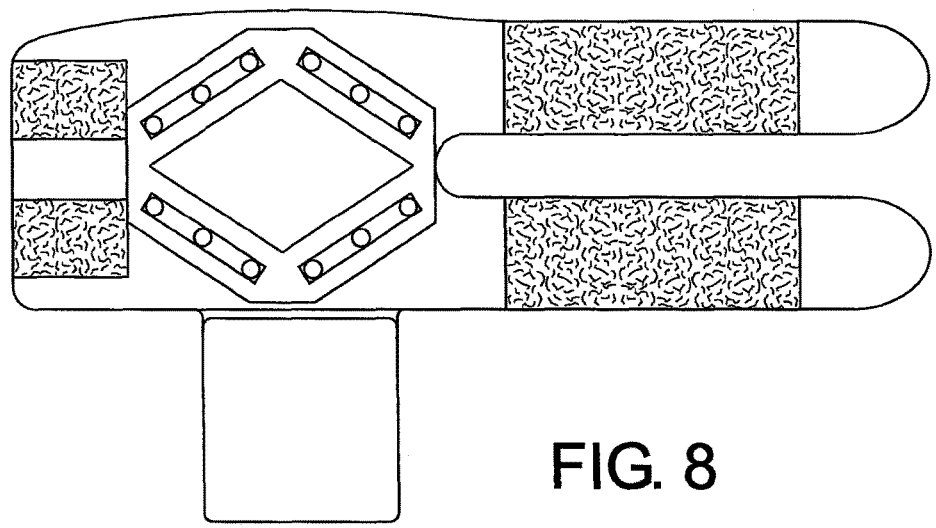
FIG. 8 is another embodiment of a knee brace.
Figure 9:
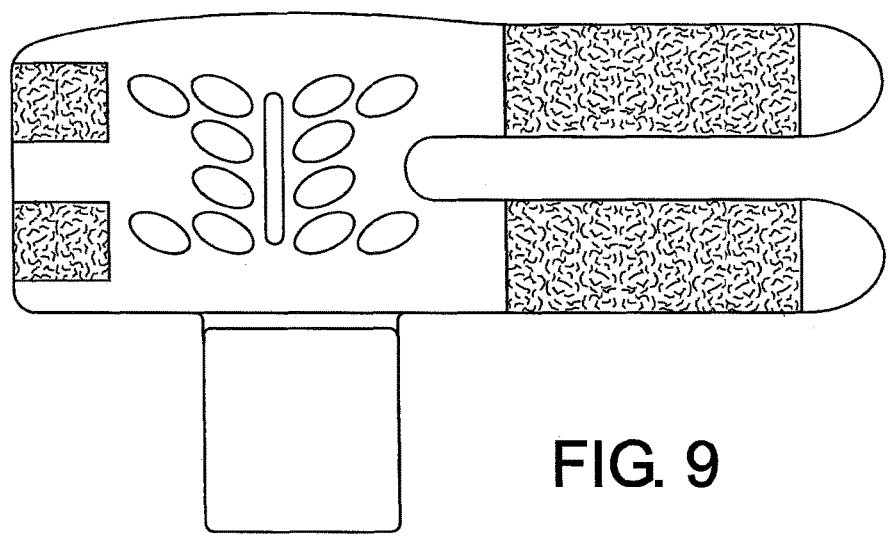
FIG. 9 is another embodiment of a knee brace.

FIGS. 8 and 9 show yet other embodiments which can also function as a wraparound knee brace including the same multi-layer structures such as is shown in FIG. 9.

In other embodiments the strip pattern can be arranged in different placements as shown in the Figures to better match treatment to the desired patient area. For example, rather than being equally spaced, the strips can be bunched together in a group, or several groups. In which case the bandage material would be constructed of a material that would allow the strips to be selectively moved and then affixed to the material at different locations. Hook-and-loop fastening fabric could accomplish this structural objective.

Figure 10:
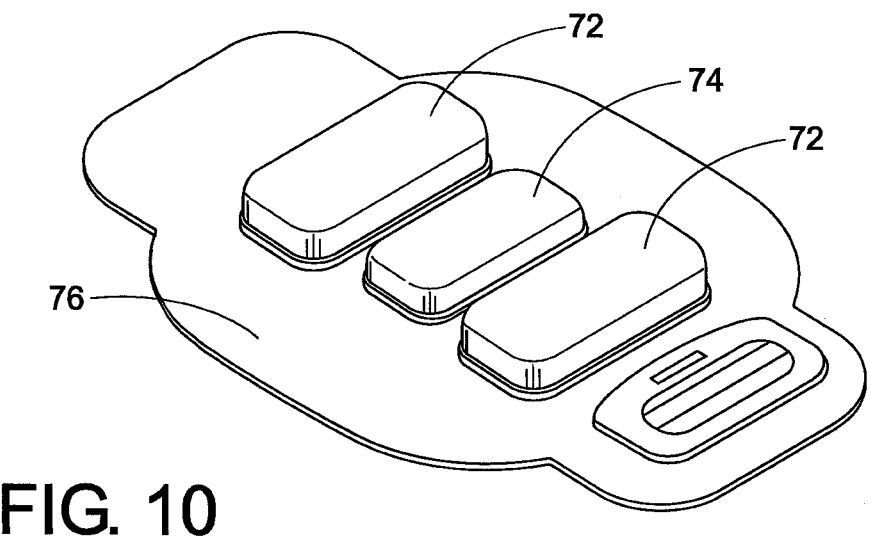
FIG. 10 is a top perspective view of one embodiment of the subject bandage system.
Figure 11:
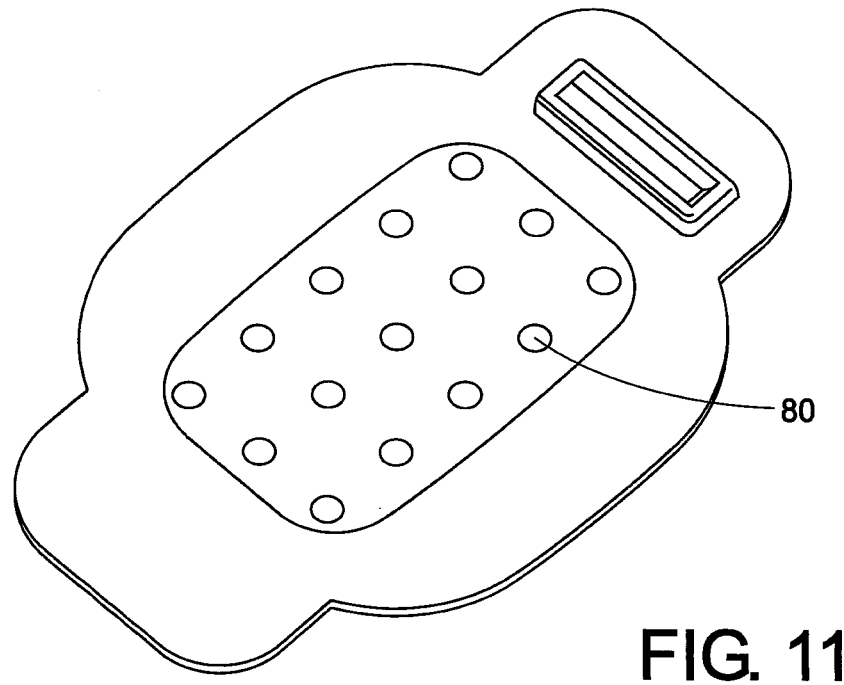
FIG. 11 is a bottom view of the device of FIG. 10.

FIGS. 10 and 11 show another embodiment wherein the battery energy sources 70 are encased in battery shrouds 72 and received with controller 74 on a primary fabric layer 76. FIG. 10 shows the top layer of the device away from a user treatment area (not shown). FIG. 11 shows the bottom surface of the device of FIG. 10 wherein the therapeutical lamps of radiation communicate to the treatment area through a plurality of spacer window openings 80.

Figure 12:
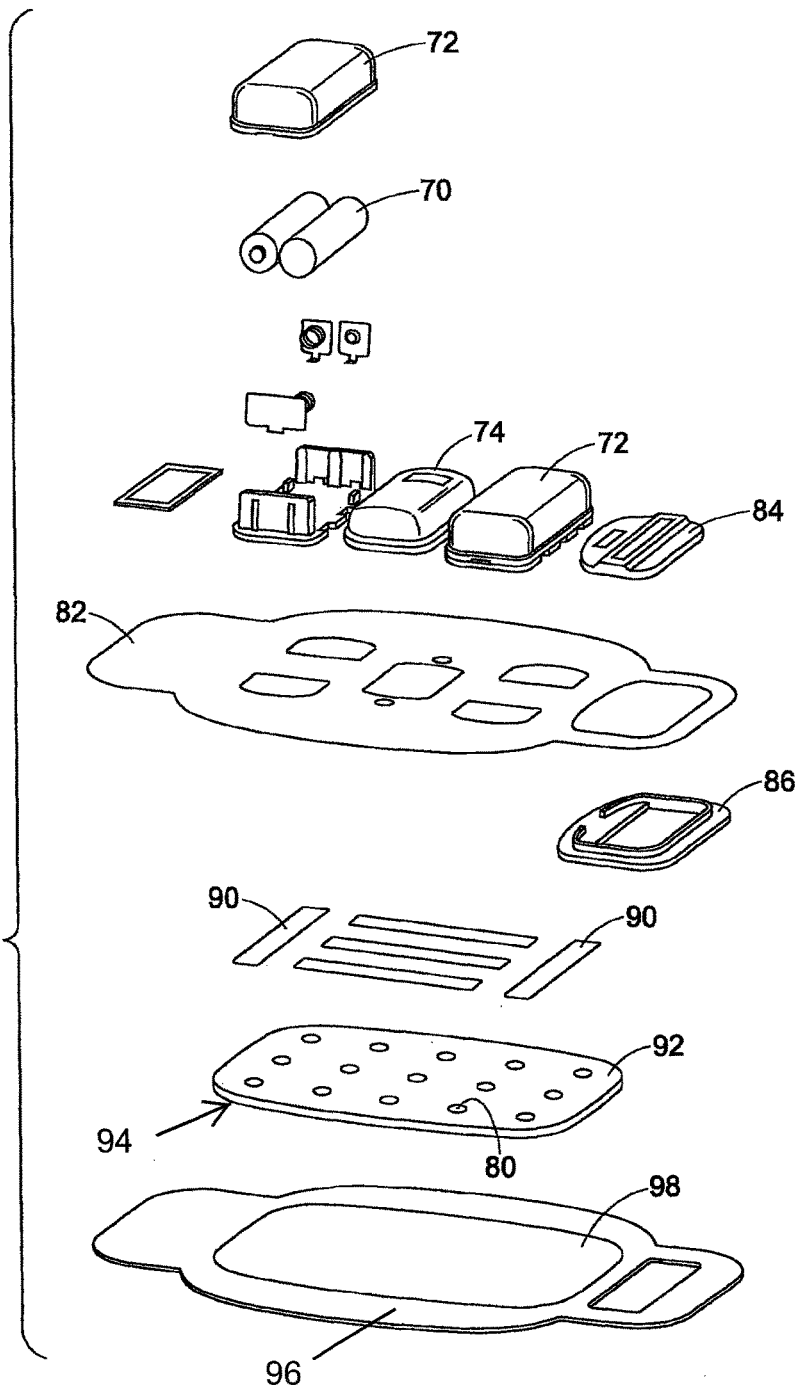
FIG. 12 is an exploded view of the device of FIG. 10.

FIG. 12 shows more clearly the component elements of the device. The battery pack 72 and controller 74 are either mechanically attached or heat bonded to the primary fabric layer 82 which can be secured to a patient treatment area through a strap (not shown) received in a buckle 84 and buckle receiver 86 assembly. The therapeutic lamps preferably comprise a plurality of LED strips 90 mounted on a foam 92 and reflective layer 94 in a manner so that the LEDs are aligned with the windows 80. Power to the LED strips 90 is communicated from the battery 72 via wires (not shown). The foam 92 and reflective layer 94 comprises a heat insulator and spacer so that the LEDs on the strips 90 are recessed relative to the opposite surface of the foam layer 92 than that on which they are mounted. The strips 90 and foam layer 92 form a subassembly that in one embodiment is selectively removable and replaceable from and to the device. Layer 92 is highly flexible as are the strips 90 so that the strip 90 and layer 92 subassembly is preferably flexible along a plurality of directions aligned with the areas intermediate the strips for the overall purpose of providing a device which is conformable to properly and comfortably cover a non-flat treatment area. The layer 92 is dimensioned so that the lamps on the LED strips 90 don't break the surface plane of layer 92 on which a reflective layer 94 is attached. Reflective layer 94 preferably comprises some type of flexible foil suitable for reflecting the radiant energy of the lamps. A secondary fabric layer 96 covers the foam 92 and reflective layer 94 with a sheer mesh 98 which allows lamp radiation to be communicated to the treatment area with minimal obstruction. The effect is that of a plurality of expanding cones of radiant energy from the lamps of the LED strips 90 that is communicated through the foam layer 92 and reflective layer 94 for therapeutic treatment of the treatment area.

The controller 74 is intended to communicate operational aspects of the device to the user in several ways. When the user actuates an on switch an indicator such as a light or beep sounder will let the user know that the device is operating. The controller will time the operation to a predetermined limit such as 10 or 15 minutes. In addition, the controller will count usage or cycle sessions to indicate to the user via a controller display of how many sessions have been run and additionally, to disable the device after the sessions have occurred so many times that the LED efficiency in generating therapeutic radiation has been so diminished that the device should no longer be used. The controller will also deactivate the indicator light after the session has been timed out or may alternatively send another sound beep to the user. Alternatively, the indicator can also provide for indicating battery life or lamp failure.

It will be appreciated that variants of the above-disclosed and other features and functions, or alternatives thereof, may be combined into many other different systems or applications. Various presently unforeseen or unanticipated alternatives, modifications, variations or improvements therein may be subsequently made by those skilled in the art which are also intended to be encompassed by the following claims.

What is claimed is:

1. A phototherapy bandage system comprising:
   a flexible primary fabric layer, the primary fabric layer including a top surface and a bottom surface;
   an insular material operatively attached to the primary fabric layer bottom surface, the insular material including a top surface facing the primary fabric layer bottom surface, a bottom surface facing away from the primary fabric layer bottom surface, and a middle region between the insular material top surface and the insular material bottom surface, the insular material including a plurality of insular material apertures extending through the insular material top surface, middle region and bottom surface;
   a radiant energy reflective layer operatively attached to the insular material bottom surface, the radiant energy reflective layer including a radiant energy reflective continuous surface facing away from the insular material bottom surface which substantially covers completely the insular material bottom surface, and includes a plurality of radiant energy reflective layer apertures extending through the radiant energy reflective layer continuous surface and aligned with the plurality of insular material apertures;
   a plurality of therapeutic lamps configured to emit radiant energy at two or more wavelengths, the plurality of therapeutic lamps attached to the insular material top surface, aligned with the plurality of insular material apertures and the plurality of reflective layer apertures, and the plurality of therapeutic lamps recessed from the radiant energy reflective surface to communicate the radiant energy from the plurality of therapeutic lamps through the insular material apertures and the radiant energy reflective layer apertures to disperse the radiant energy over a user treatment area, and the radiant energy reflective layer further dispersing over the user treatment area radiant energy reflected from the user treatment area to the radiant energy reflective layer back to the user treatment area; and
   a controller operatively connected to the plurality of therapeutic lamps and configured to control the plurality of therapeutic lamps.

2. The system of claim 1 wherein the insular material includes a foam layer spacing the lamps from the user treatment area.

3. The system of claim 1 further comprising:
   a battery and a controller operatively associated with the plurality of therapeutic lamps.

4. The system of claim 1 wherein the flexible primary fabric layer is flexible and compliant to conform to the user treatment area.

5. The system of claim 3 wherein the plurality of therapeutic lamps, the battery and the controller are disposed on the primary fabric layer for system flexibility in a plurality of directions for enhanced conformance of the bandage system to the user treatment area.

6. The system of claim 1 further comprising a cover material including a sheer mesh layer attached to the radiant energy reflective surface.

7. A radiant energy bandage system comprising:
   a flexible primary fabric layer, the primary fabric layer including a top surface and a bottom surface;
   an insular material operatively attached to the primary fabric layer bottom surface, the insular material including a top surface facing the primary fabric layer bottom surface, a bottom surface facing away from the primary fabric layer bottom surface, and a middle region between the insular material top surface and the insular material bottom surface, the insular material including a plurality of insular material apertures extending through the insular material top surface, middle region and bottom surface;
   a radiant energy reflective layer operatively attached to the insular material bottom surface, the radiant energy reflective layer including a radiant energy reflective continuous surface facing away from the insular material bottom surface which substantially covers completely the insular material bottom surface, and includes a plurality of radiant energy reflective layer apertures extending through the radiant energy reflective layer continuous surface and aligned with the plurality of insular material apertures;
   a plurality of therapeutic lamps configured to emit radiant energy at two or more wavelengths, the plurality of therapeutic lamps attached to the insular material top surface, aligned with the plurality of insular material apertures and the plurality of reflective layer apertures, and the plurality of therapeutic lamps recessed from the radiant energy reflective surface to communicate the radiant energy from the plurality of therapeutic lamps through the insular material apertures and the radiant energy reflective layer apertures to disperse the radiant energy over a user treatment area, and the radiant energy reflective layer further dispersing over the user treatment area radiant energy reflected from the user treatment area to the radiant energy reflective layer back to the user treatment area;
   a controller for operating the plurality of therapeutic lamps; and
   an energy source to power the plurality of therapeutic lamps and the controller.

8. The bandage system of claim 7 wherein the plurality of lamps include a plurality of LED strips attached to the insular material.

9. The bandage system of claim 7 wherein the insular material is selectively removable and replaceable.

10. The bandage system of claim 7 wherein the controller includes a timer for limiting on-time and use cycles of the plurality of therapeutic lamps.

11. The bandage system of claim 7 wherein the plurality of therapeutic lamps, the controller and the energy source are disposed on the flexible primary fabric layer for system flexibility in a plurality of directions for enhanced conformance of the bandage system to the user treatment area.

12. The phototherapy bandage system according to claim 1, wherein the plurality of lamps include a plurality of LED strips attached to the insular material top surface.

13. The phototherapy bandage system according to claim 1, wherein the insular material is selectively removable and replaceable.

14. The phototherapy bandage system according to claim 1, wherein the plurality of therapeutic lamps are configured to emit the radiant energy at one or both of a blue and red wavelength.

15. The radiant energy bandage system according to claim 7, further comprising a cover material including a sheer mesh layer attached to the radiant energy reflective surface.

16. The radiant energy bandage system according to claim 7, wherein the plurality of therapeutic lamps are configured to emit the radiant energy at one or both of a blue and red wavelength.

* * * * *